United States Patent [19]

Charlton et al.

[11] Patent Number: 5,759,364
[45] Date of Patent: Jun. 2, 1998

[54] ELECTROCHEMICAL BIOSENSOR

[75] Inventors: Steven C. Charlton, Osceola; Yingping Deng, Granger, both of Ind.; Karl-Heinz Hildenbrand, Krefeld, Germany; Larry D. Johnson, Elkhart; James J. Venosky, Goshen, both of Ind.

[73] Assignee: Bayer Corporation, Elkhart, Ind.

[21] Appl. No.: 850,608

[22] Filed: May 2, 1997

[51] Int. Cl.⁶ ............................................. G01N 27/26
[52] U.S. Cl. .................. 204/403; 435/817; 435/287.1; 435/289.1; 156/102; 156/106; 156/107; 156/196; 156/217; 156/219; 156/220
[58] Field of Search ................. 204/403; 435/817, 435/287.1, 289.1; 156/102, 106, 107, 196, 217, 219, 220

[56] References Cited

U.S. PATENT DOCUMENTS

| | | | |
|---|---|---|---|
| 5,512,159 | 4/1996 | Yoshioka et al. | 204/403 |
| 5,582,697 | 12/1996 | Ikeda et al. | 204/403 |
| 5,628,890 | 5/1997 | Carter et al. | 204/403 |

*Primary Examiner*—Bruce F. Bell
*Attorney, Agent, or Firm*—Jerome L. Jeffers

[57] ABSTRACT

Disclosed is an electrochemical sensor which is made up of an insulating base plate bearing an electrode on its surface which reacts with an analyte to produce mobile electrons. The base plate is mated with a lid of a deformable material which has a concave area surrounded by a flat surface so that when mated to the base plate there is formed a capillary space into which a fluid test sample can be drawn. The side of the lid facing the base is coated with a polymeric material which serves to bond the lid to the base plate and to increase the hydrophilic nature of the capillary space.

20 Claims, 1 Drawing Sheet

ELECTROCHEMICAL BIOSENSOR

BACKGROUND OF THE INVENTION

The present invention relates to an electrochemical biosensor that can be used for the quantitation of a specific component (analyte) in a liquid sample and, more specifically, to a method of manufacturing such a biosensor. Electrochemical biosensors of the type under consideration are disclosed in U.S. Pat. Nos. 5,120,420 and 5,264,103. The devices disclosed in these patents have a plastic base upon which carbon electrodes are printed which electrodes are covered with a reagent layer which comprises a hydrophilic polymer in combination with an oxidoreductase specific for the analyte. There is typically a spacer element placed on the base, which element is cut out to provide a generally U shaped piece and a cover piece, so that when the base, spacer element and cover piece are laminated together, there is created a capillary space containing the electrodes and the reagent layer. In addition to the oxidoreductase, there is included an electron acceptor on the reagent layer or in another layer within the capillary space. A hydrophilic polymer, e.g. carboxymethyl cellulose, is used to facililtate the drawing of the aqueous test fluid into the capillary space.

There has been developed more recently an electrochemical sensor which is comprised of two parts; a lower part (base) which carries the electrode structure with an oxidoreductase and electron acceptor evenly distributed in a hydratable polymeric matrix on the electrodes' surface, and an upper part (lid) which is embossed to form three sides of a capillary space with the base forming the fourth side upon mating of the lid and base. The base and lid are laminated together by means of a heat activated adhesive coating on the lid. The sensor is used by dipping the open end of the capillary into a small drop of test fluid, such as blood, which is drawn into the capillary tube so that it covers the enzyme and electron acceptor on the electrode's surface. Due to the hydratable nature of the polymer matrix, it disperses in the aqueous test fluid thereby allowing the oxidoreductase, which is glucose oxidase when the sensor is designed to determine the concentration of glucose in blood, to oxidize the analyte and the electron acceptor to shuttle the excess electrons to the working electrode thereby creating a measurable current which is proportionate to the concentration of analyte in the test fluid.

The manufacture of the prior art sensors as described above involves the use of an extra part, the spacer layer, and a number of processing steps which are not required with the two part sensor (base and lid) with which the present invention is involved. This type of sensor is prepared by a straight forward procedure which involves the steps of:

a) printing the electrodes onto the base material, b) coating the electrodes with the polymeric matrix containing the oxidoreductase and the electron acceptor, c) coating the bifunctional adhesive layer of the present invention onto the lid, d) embossing the capillary channel into the lid, and e) heat sealing the lid onto the base.

There is presented a two-fold problem in preparing a sensor of this type. The first relates to providing a sensor whose capillary space is rapidly filled with the test fluid and the second is to facilitate assembly of the sensor by adhering the lid to the base. In order to accomplish this in a manner which permits the rapid assembly of a large quantity of sensors, it was necessary to prepare a coating for application to the lid which:

i. adheres strongly to the lidstock material, ii. is pliable and extensible enough to survive embossing into three sides of the lid, iii. enables rapid filling of the capillary space, iv. enables filling over a base having a relatively hydrophobic surface (contact angle up to 90°), v. enables filling with blood having hematocrits of from 0 to 60% when blood is the test fluid, vi. is non-tacky under ambient conditions, vii. capable of being activated and sealed by heat applied through the lid from a hot plate, ca. 165° C., viii. is capable of forming a good bond with the surface of the base material, ix. will not interfere when individual sensors are excised from a tight array, and x. maintains the above properties for a period of time sufficient to provide a sensor with adequate shelf life.

SUMMARY OF THE INVENTION

The present invention is an electrochemical sensor for the detection of an analyte in a fluid test sample which comprises:

a) an insulating base plate;

b) an electrode layer on the base plate in operative connection with an enzyme which reacts with the analyte to produce mobile electrons; and c) a lid of deformable material which has been embossed to provide a concave area in a portion thereof while leaving a flat surface surrounding the concave portion in such a manner that, when mated with the base, the lid and base form a capillary space in which the enzyme is available for direct contact with the fluid test sample which is drawn into the capillary space by capillary action, wherein said sensor has a layer of a water dispersible polyurethane over the underside of the lid to facilitate bonding of the lid to the base upon the lid and base being mated and to increase the hydrophilic nature of the capillary space to thereby increase the rate at which blood will flow into it.

DESCRIPTION OF THE INVENTION

Figure 1:
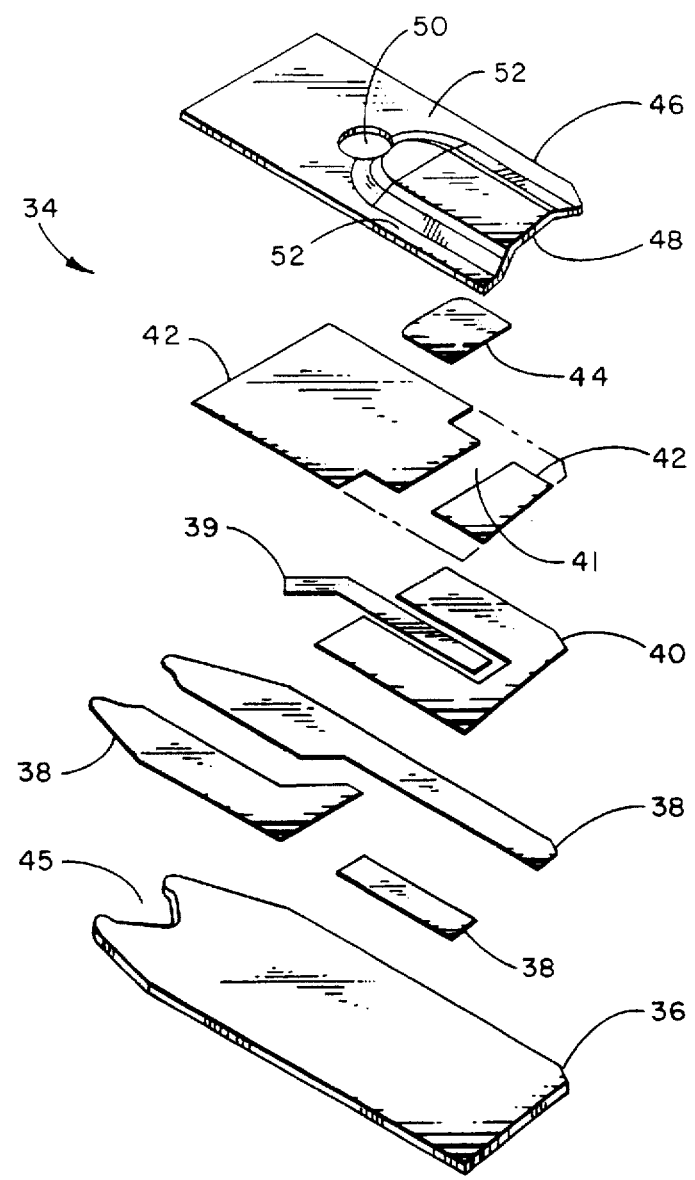
FIG. 1 represents the construction of the sensor of the present invention.

The construction of the sensor with which the present invention is concerned is illustrated by FIG. 1. The sensor 34 is comprised of insulating base 36 upon which is printed in sequence (by screen printing techniques), an electrical conductor pattern 38, an electrode pattern (39 and 40), an insulating (dielectric) pattern 42 and finally a reagent layer 44. The electrical conducting pattern 38 is optional, but its presence in the sensor is preferred to reduce the overall resistance of the sensor. The function of the reagent layer is to convert glucose, or another analyte, stoichiometrically into a chemical species which is electrochemically measurable, in terms of current it produces, by the components in the electrode pattern. The two parts 39 and 40 of the electrode print provide the two electrodes necessary for the electrochemical determination. The electrode ink, which is about 14μ (0.00055") thick, contains electrochemically active carbon. Components of the conductor ink are typically a mixture of carbon and silver, chosen to provide a low electrical resistance path between the electrodes and the meter with which they are in operative connection, via contact with the conductor pattern at the fish-tail end of the sensor 45. The typical thickness of the entire structure is 6μ (0.00025"). The function of the dielectric pattern is to enhance the reproducibility of the sensor reading by insulating the electrodes from the test sample except in a defined area 41 of the electrode pattern. A defined area is important in this type of electrochemical determination because the measured current is dependent both on the concentration of the analyte and the area of the electrode which is exposed to the analyte containing test sample. A typical dielectric layer comprises a UV cured acrylate modified polyurethane about 10μ (0.0004") thick. The typical thickness of the electrode structure is 6μ (0.00025"). The lid 46, which is embossed to provide a concave space 48 and punctured to provide air vent 50, is joined to the base 36 in a heat sealing operation. The base and lid are first aligned and then pressed together by means of a heated metal plate which is shaped such that contact is made only with the flat, non-embossed regions of the lid 52. The water dispersible polyurethane layer on the bottom surface of the lid is thereby melted and serves to fuse the lid 46 and the base 36 together upon cooling. A typical temperature for the heated plate is 165° C. with the pressure being 2200 p.s.i. Holding the lid and base together under these conditions of heat and pressure for 1¼ seconds provides the desired unitary sensor with the capillary space for acceptance of the fluid test sample. The polyurethane layer bonds to the topmost exposed layer (dielectric 42 with dotted edges) of the base under the flat regions of the lid. Alternatively, the edges of the dielectric are slightly narrowed (represented by dielectric layer 42 with solid edges) which allows the polyurethane to bond with the material of the electrode print pattern 40. This is a preferred configuration because the bond strength between the polyurethane adhesive and the electrode ink is greater than that between the adhesive and the dielectric material thereby providing a more leakproof capillary space.

Suitable materials for the insulating base include polycarbonate, polyethylene and dimensionally stable vinyl and acryl polymers as well as polymer blends such as polycarbonate/polyethylenentherephthalate. The lid is typically fabricated from a deformable polymeric sheet material such as polycarbonate or an embossable grade of polyethyleneterephthalate or glycol modified polyethylene terephthalate, whereas the dielectric layer can be fabricated from an acrylate modified polyurethane which is curable by ultra-violet (UV) light, a polyurethane which is curable by UV light or moisture or a vinyl polymer which is heat curable.

The water dispersible polyurethane layer on the underside of the lid serves to increase the hydrophilic nature of the capillary space and to facilitate its close adherence to the base either by bonding to the dielectric layer or to the electrode material.

The present invention facilitates the use of an embossed lid (46, FIG. 1) as opposed to the use of a spacer as in the prior art sensor elements in which, instead of embossing, the two sides of the capillary space are formed from a cutout in a spacer material which also carries a pressure sensitive adhesive to adhere the base to the spacer and the spacer to the lid. The use of the embossed lid enables one to avoid the use of an extra part, i.e. the spacer, and a number of processing steps. The steps involved in assembling the spacer containing sensor are:

i. preparing the complete electrode structures including the reagent layer; an agent to induce wicking of blood into the capillary space needs to be included in the uppermost layer;

ii. adding an additional layer containing an agent to induce wicking of blood into the capillary space; this layer may be avoided if the agent is included in the chemistry layer;

iii. die cut a capillary channel into the spacer material which is typically a laminate of release/liner/adhesive/ spacer material/adhesive/ release liner;

iv. strip the release liner from one side of the spacer material and attach the spacer to the base; and v. strip the release liner and assemble the lid to the other side of the spacer.

The present invention permits one to manufacture a sensor by:

i. printing electrodes onto the base material;

ii. coating the bifunctional layer onto the under surface of the lid;

iii. embossing the top and sides of the capillary space into the lid;

iv. mating the lid to the base and sealing them together by the application of heat and pressure.

The bifunctional coating of the present invention provides a non-tacky adhesive as opposed to the tackiness of a pressure sensitive adhesive. Accordingly, there is no need to remove and dispose of a release liner before assembly and there is a dramatic reduction in the problems associated with the sensor assembly equipment being fouled by the adhesive material. Accordingly, the sensors of the present invention can be manufactured by mating an array of lids with a corresponding array of bases and then excising individual sensors from the array by a punching process. A tacky, pressure sensitive adhesive would be incompatible with this punching step due to adhesive buildup in the dies which would necessitate frequent cleaning and lost production time.

The water dispersible polyurethanes of the present invention are capable of being laid down on the lid stock in a pattern to form a non-tacky layer under ambient conditions. They can be activated for fusing to the base at a temperature sufficiently low to avoid damage to the reagents in the reagent layer while forming a good bond with desirable lid materials which are long lasting thereby providing good shelf life. The coating also increases the hydrophilic nature of the interior of the capillary space due to its ionomeric property which presumably causes the surface to be significantly ionic in character. Based on these dual properties the water dispersible polyurethane can be referred to as a bifunctional coating material.

The reaction of a diisocyanate with equivalent quantities of a bifunctional alcohol such as glycol gives a simple linear polyurethane. These products are unsuitable for use in the manufacture of coatings, paints and elastomers. When simple glycols are first reacted with dicarboxylic acids in a polycondensation reaction to form long chain polyesterdiols and these products which generally have an average molecular weight between 300 and 2000 are subsequently reacted with diisocyanates the result is the formation of high molecular weight polyester urethanes. Polyurethane dispersions have been commercially important since 1972. Polyurethane ionomers are structurally suitable for the preparation of aqueous two-phase systems. Those polymers which have hydrophilic ionic sites between predominately hydrophobic chain segments are self-dispersing and, under favorable conditions, form stable dispersions in water without the influence of shear forces and in the absence of dispersants. One method of preparing cationic urethanes is by the reaction of a dibromide with a diamine. If one of these components contains a long chain polyether segment, an ionomer is obtained. Alternatively, polyammonium-polyurethanes can be made by first preparing a tertiary nitrogen containing polyurethane and then quaternizing the nitrogen atoms in a second step. Starting with polyether based NCO prepolymers, segmented quaternary polyurethanes are obtained. Similarly, cationic polyurethanes with tertiary sulphonium groups can be prepared when the tert.-aminoglycol is substituted for thiodiglycol. The ionic moiety or its precursor can also be the diisocyanate or part of a long chain polyetherdiol.

In order to obtain anionic polyurethanes, diols bearing a carboxylic acid or a sulphonate group are usually introduced and the acid groups subsequently neutralized, for example with tertiary amines. Sulphonate groups are usually built via a diaminoalkanesulphonate, as these compounds are soluble in water and reaction with NCO prepolymers is not adversely affected by water. The resulting polyurethane resins have built in ionic groups which provide mechanical and chemical stability as well as good film forming and adhesion properties.

The most important property of polyurethane ionomers is their ability to form stable dispersions in water spontaneously under certain conditions to provide a binary colloidal system in which a discontinuous polyurethane phase is dispersed in a continuous aqueous phase. The diameter of the dispersed polyurethane particles can be varied between about 10 and 5000 nm.

Solutions of polyurethane ionomers in polar solvents such as acetone, methyl ethyl ketone and tetrahydrofuran spontaneously form dispersions when water is stirred in. The organic solvent can then be distilled off to give solvent-free sols and latices of the ionomers. Depending on the content of ionic groups and the concentration of the solution, the ionomer dispersion is formed by precipitation of the hydrophobic segments or by phase inversions of an initially formed inverse emulsion.

In converting an organic solution into an aqueous dispersion a 2000 molecular weight polyester based on adipic acid is reacted with excess hexamethylenediisocyanate to give an NCO terminated prepolymer. After the addition of an equal molar amount of N-methyldiethanolamine dissolved in acetone, the viscosity increases while polyaddition proceeds. As the viscosity increases, additional amounts of acetone are added to keep the mixture stirrable. The tertiary nitrogen containing segmented polyurethane is now quaternized with dimethyl sulphate. Formation of the polyurethane ionomer results in further increase in viscosity. The ionic centers associate in a manner similar to that of soaps in paraffin oil with an apparent increase in molecular weight. When water is slowly added to such an ionomer solution the viscosity decreases during the addition of the first few milliliters of water. Apparently, the ionic association is reversible and any water present reduces the ionic association to provide a clear solution in which the ionomer is molecularly dispersed. As more water is added, the viscosity increases again although the polymer concentration decreases. This is the first phase of the formation of the dispersion. Further addition of water produces a turbidity, indicating the beginning of the formation of a dispersed phase. Further addition of water increases turbidity and finally the viscosity drops, since, due to the further decrease of acetone concentration, the agglomerates have been rearranged to form microspheres. In this state there is a continuous water phase and a discontinuous phase of polyurethane particles which are swollen by acetone.

The final step in preparing the aqueous dispersion is the removal of acetone by distillation. The turbidity increases and the viscosity decreases due to the polymer chain recoil or shrinkage.

The physical properties of the dispersion depend on a variety of parameters such as chemical composition, type and amount of ionic group, molecular weight and method of preparation. The diameter of the particles will vary from about 10 nm to 5 µm and the appearance of the dispersion can vary between an opaque translucent sol and a milky white dispersion. The viscosity and Theological properties can also vary within wide limits, including Bingham type viscosity and rheopexy.

Ionomers are excellent dispersants. The acetone process works well even if only a fraction of the polyurethane is ionic since this part of the material will form the outer shell of the relatively course latex particles.

The above procedure for the preparation of polyurethane dispersions is universal; all linear polyurethanes which can be synthesized in organic solvents may be modified with ionic groups. Because of its low boiling point and low toxicity, acetone is particularly suitable for preparing polyurethane dispersions.

The construction of a sensor according to the present invention is accomplished according to the following general example:

GENERAL EXAMPLE

In this example, a large number of sensor lids are fabricated from a rolled sheet of polycarbonate which has been unrolled to provide a flat surface. This sheet is referred to as the lid stock since it will be the source of a multiplicity of lids.

A bifunctional coating solution, comprising an aqueous polyurethane dispersion, is spread on to one side of a polycarbonate sheet (0.0075"/175µ thick) using a wire wound rod or a slot die coater and air dried. The dried coating thickness is in the range of 0.0007" to 0.002" (17µ to 50µ) with the wet coating thickness in the range of 0.0014" to 0.005" (35µ to 125µ) for a typical solids content of 40% to 50%. Drying can be at ambient temperature or by forced drying under a stream of air at 70° C. The bifunctional layer has some tack for a short period after drying and when the sheet is rewound a temporary liner or interleave is introduced in contact with the coating and, the coating is in contact with the liner of the polycarbonate. After a period of a few hours, the initial tack is lost allowing the polycarbonate lid stock to be unrolled without damage to the coating. Suitable materials for the liner are polyolefins or polyethyleneterephthalate in a thickness of from 0.001 to 0.003" (25–75µ).

The next stage of processing involves embossing of the concave areas of the lids and the punching of various holes in the polycarbonate sheet for registration and tracking. The sheet is then slit longitudinally to give a ribbon of sensor lids in a line which is then rolled up. It is essential that the adhesive be non-tacky so that it sticks to neither the embossing and punching tools nor to the reverse side of the polycarbonate support while rolled in ribbon form. It is also essential that the adhesive not form gummy deposits on the punching or embossing tools which would necessitate frequent cleaning.

The base stock, typically of polycarbonate, is printed with various inks to form the electrodes and then overcoated with a dielectric layer in a predetermined pattern designed to leave a desired surface of the electrode exposed. The bifunctional material must adhere to the dielectric material when the lid is mated directly to the dielectric layer. In order to assemble the lidstock to the base, the continuous ribbon of lid stock is unwound and passed through a special laminator where it is registered and then combined with a strip of the base stock under the influence of heat and pressure. It is desirable for the heat sealing process to take about one second which requires an adhesive which is capable of very rapidly forming a strong bond. After heat sealing, the continuous ribbon of laminate is wound onto a reel.

In order to singulate individual sensors from the laminate ribbon, the laminate is passed through punching equipment in which individual sensors are punched from the ribbon and then placed in a buffer preparatory to being placed into a foil blister package for storage. Here again, it is essential that the adhesive not gum or cold flow onto and form deposits in the punch mechanism. It is also essential that the adhesive be tack free so that the sensor not stick to the punch and reliably transfer to the buffer and from the buffer to the blister package from which it will be dispensed. Accordingly, the coating's melting point must be high enough to prevent accidental melting and resultant tack from frictional heating during the melting process. Furthermore, the adhesive bond strength between the lid stock and the base stock must be strong enough to withstand delamination peel forces generated during this punch operation.

In the preferred method of using the sensors, they are packaged in a circular disk having ten individual compartments (blisters) arranged radially. The disk is made from an aluminum foil/plastic laminate which is sealed to isolate the sensor from ambient humidity and from other sensors with a burst foil cover, which disk is mounted within a specially designed instrument. The sensor is kept dry by a desiccant located inside the individual compartments. To retrieve a sensor, a knife is driven down through the burst foil into an individual elongated compartment at the end closest to the hub of the disk and then moved radially toward the perimeter of the blister. In doing so, the knife engages the rear (fish tail) of the sensor in that compartment. Radial travel of the knife pushes the tip of the sensor out through the burst foil and through parts of the instrument such that the nose of the sensor is completely out of the instrument and ready to receive a fluid test sample, e.g. blood. For this stage, it is essential that the bond between the base and lid of the sensor withstand the sheer forces generated when the sensor bursts out through the foil. This method of providing a sensor ready for use is more fully described in U.S. Pat. No. 5,575,403.

Finally, the sensor tip, containing the opening to the capillary space, is touched to a small drop of the fluid test sample which is typically blood produced by a finger prick. The blood is rapidly drawn up into the capillary where the interaction with the enzyme is initiated and the instrument is signaled to initiate its timing sequence. It is essential that blood be drawn very rapidly into the capillary space, regardless of its spatial orientation in order that the timing sequence be initiated.

The bifunctional coating of the present invention is based on a water dispersible polyurethane prepared as previously described. A particularly useful formulation is Dispercoll U 53 BC, from Bayer AG, which is a linear aliphatic polyester urethane based on hexamethylene diisocyanate (HDI) and isophorone diisocyanate (IPDI) in aqueous dispersion with a mean particle size of 100 nm. This product, whose total weight % solids in aqueous dispersion is 40±1, has a viscosity at 73° F./23° C. (cps/mpa) (Brookfield LVF, spindle 2, 30 rpm) of <600. The white liquid dispersion has a specific gravity of 1.2 g/cm$^3$ and the polymer exhibits a high level of crystallization. The dispersion's specific gravity is 1.1, its pH is 7 and it carries an anionic particle charge. The manufacturers recommend that it be kept at a pH of 6–8 since acidic or highly alkaline conditions can cause a loss of properties due to hydrolytic degradation of the polymer.

Dispercoll U, the tradename for a range of aqueous, colloidal dispersions of high molecular weight hydroxyl polyurethane polymers, are preferred for use in the present invention. Because they are prepared by the previously described ionomer process, these dispersions contain only small quantities of emulsifiers while still exhibiting outstanding mechanical and chemical stability.

Various other materials can be combined with the urethane dispersion to enhance the properties of adhesion and hydrophilicity which make it useful in the manufacture of sensors. The addition of surfactants will increase the wettability of the surface of the dried polyurethane film to enhance the ability of test fluids such as blood to enter the capillary space. Thus, the addition of surfactants such as the sodium salt of an octylphenoxypolyethoxyethyl sulfate (Triton® W30), a fluorocarbon such as an amine perfluoroalkyl sulfonate (Fluorad™ FC 99), a potassium salt of a fluoroalkyl carboxylate (Fluorad™ FC 129) or an anionic or a neutral fluorosurfactant such as Zonyl® FSA or Zonyl® FSN is useful to increase the ability of the capillary space to draw in test fluid and to avoid defects during the coating procedure by improving the wetting of the substrate. There is an optimal range of concentration for each surfactant, i.e. enough to provide good hydrophilic nature in the capillary space of the sensor but not enough to reduce the bond strength between the lid and base. Concentrations typically range from 0.05% to 0.2% by weight of the polyurethane dispersion.

The addition of a secondary polymer or co-polymer such as Airflex® 400 vinylacetate-ethylene copolymer, Elvace® 40705 or 40722 in amounts up to about 33 weight % of the dispersion can be used to strengthen the bond between the lid and the layer of dielectric material. Vinyl acetate copolymers, such as Flexbonde® 150 from air products can also be used in an amount of up to about 10 weight % of the dispersion to enhance bond strength between the lid and the dielectric layer. This is especially true when the dielectric layer contains silicone additives as defoamers.

Thickeners, such as Acrysol RM-8, which is a polyurethane associative thickener, can be added to the dispersion in order to raise its viscosity for easier coating and prevent cracking of the polyurethane layer during drying. A coloring agent, such as Erioglaucine from Sigma Chemical Company, a water soluble blue chromophore, can be added to the coating material as a visualizing agent. The following Table A sets out 8 formulations for the bifunctional coating which are useful in fabricating the sensor with which this invention is concerned.

TABLE A

| REAGENT | CONCN (%) | FORMULATION NUMBER | | | | | | | |
|---|---|---|---|---|---|---|---|---|---|
| | | 1 | 2 | 3 | 4 | 5 | 6 | 7 | 8 |
| U 54 | 50 | 21.37 | 21.71 | 21.37 | 19.24 | 14.58 | 14.58 | 14.58 | 14.58 |
| FLEXBOND 150 | 55 | 6.47 | 6.58 | 6.47 | | 6.63 | 6.63 | 6.63 | 6.63 |
| AIRFLEX A400 | 55 | | | | 8.75 | | | | |
| ELVACE 40705 | 55 | | | | | 6.63 | 6.63 | | |
| ELVACE 40722 | 55 | | | | | | | 6.63 | 6.63 |
| RM-8 | 1 | 1.5 | 1.5 | 1.5 | 1.5 | 1.5 | 1.5 | 1.5 | 1.5 |
| ZONYL FSN | 10 | 0.6 | | | | 0.6 | | 0.6 | |
| ZONYL FSA | 10 | | 0.15 | | 0.45 | | | | |
| FLUORAD FC-129 | 10 | | | 0.6 | | | 0.6 | | 0.6 |
| ERIOGLAUCINE | 5 | 0.06 | 0.06 | 0.06 | 0.06 | 0.06 | 0.06 | 0.06 | 0.06 |
| TOTAL | | 30 | 30 | 30 | 30 | 30 | 30 | 30 | 30 |

The present invention is further illustrated by the following examples:

EXAMPLE 1

Water Dispersible Polyurethane U53 as the Bifunctional Layer.

Components were combined in the order shown in Table 1 with thorough mixing.

TABLE 1

| Component | Function | Concn (%) | Amount (g) | Dry compsn. (%) |
|---|---|---|---|---|
| U 53 polyurethane | adhesive | 40 | 291 | 99.9 |
| erioglaucine | colorant | 5 | 0.58 | .025 |
| Aervsol RM-8 | thickener | 1 | 8.18 | .07 |

The solution was allowed to stand for a number of hours to allow entrapped bubbles to escape and was then coated onto a polycarbonate sheet (0.0075"/190μthick) using a #38 wire wound rod to give a wet thickness of 0.0013 inch. After drying at 50° C. for 3 minutes under a stream of air heated to 60°, the film of the dry composition was 0.0013 inch/35μ thick. This film was tacky but could be rolled up with a polyethylene interleave. After a period of several hours this interleave was removed without damage to the film leaving a smooth, non-tacky surface. This material was then punched and formed in mechanical tools to generate the embossed concave shape of the lid as depicted in FIG. 1. A polycarbonate insulating base was sequentially printed with the following inks: a conductor pattern using polymer thick film composition 5085 from duPont; a dielectric pattern using polymer thick film composition 7102T, also from dupont, a dielectric pattern using RDMSK 4954 from Norcote. This dielectric normally contains a small amount of the surfactant Silwet® 77. For experimental purposes, some printings were made without this surfactant. The embossed lidstock was aligned with the appropriate region of base material and heat sealed with a hot plate at a temperature of 165° with the application of about 2000 p.s.i. for a time of 1 second. The lid stock was fused directly to the dielectric coating on the base.

The completed sensor was mounted vertically with the capillary opening facing downward and a small drop of blood (7 μL) was raised to just touch the opening. The time taken for the blood to travel vertically upwards from the front to the rear of the capillary (a distance of 4 mm) was measured by means of a video camera. The filling times are set out in Table 2.

In order to measure the peel strength of the bond between the lid and dielectric layer on the base, a 0.2 inch×0.4 inch sealed area between the lidstock and the base was carried out by holding the base and peeling off the lidstock at an angle of 90°. The mean force in p.l.i. (pounds per linear .inch) necessary to do this was measured and is set out in Table 2.

TABLE 2

| Peel strength (p.l.i.) | Dielectric surfactant | Sample hematocrit | Filling time(s) after 10 weeks under the following storage conditions. | | | |
|---|---|---|---|---|---|---|
| | | | Initial | 4° | 40° | 50° |
| 8 | none | 40 | 0.46 | 0.25 | 0.38 | 1.23 |
| | .075% L-77 | 40 | 0.36 | 0.35 | 0.48 | 1.15 |

In this experiment the base had no reaction layer. Nevertheless, there was exhibited strong bond strength and a very rapid fill time over the storage conditions of 4° to 40°. Inclusion of the surfactant Silwet® L-77 in the dielectric layer had a negligible effect.

EXAMPLE 2

Water Dispersible Polyurethane Combined with the Secondary Polymer Flexbond® 845.

The film was prepared and tested as in the previous example with the results being set out in Tables 3 and 4. The test results show good bond strength and rapid blood filling even at high hematocrit when stored at refrigerator temperatures. The vinyl-acrylate copolymer is optional in conjunction with the bifunctional coating material of the present invention. It can be used advantageously in situations such as those in which the dielectric layer does not form a long lasting bond with the polyurethane.

TABLE 3

| Component | Function | Concn (%) | Amount (g) | Dry compsn. (%) |
|---|---|---|---|---|
| U 53 polyurethane | adhesive | 40 | 278 | 93.7 |
| Flexbond 845 | adhesive | 55 | 13.4 | 6.2 |
| erioglaucine | colorant | 5 | 0.6 | .025 |
| Aervsol RM-8 | thickener | 1 | 7.5 | .06 |

TABLE 4

| Peel strength (p.l.i.) | Dielectric surfactant | Sample hematocrit | Filling time(s) after 13 weeks under the following storage conditions. | | | |
|---|---|---|---|---|---|---|
| | | | Initial | 4° | 40° | 50° |
| 7.7[1] | .075% L-77 | 40 | 1.02 | 0.65 | 3.6 | 3.6 |
| | | 60 | 1.12 | 0.97 | 2.5 | 4.3 |

[1]Dielectric contained no surfactant.

EXAMPLE 3

Water Dispersible Polyurethane U53 with the Surfactant Triton® W30.

This film was prepared as in the previous examples with the components being added in the order shown. Fill times with the superscript 1 correspond to sensors without the reagent layer which were tested after 10 weeks storage. Those sensors with the superscript 2 had printed reagent layers of glucose oxidase/potassium ferricyanide in poly(ethylene oxide) beneath the dielectric layer and partially exposed through the opening in this layer. The results of this experiment are set out in Tables 5 and 6.

TABLE 5

| Component | Function | Concn (%) | Amount (g) | Dry compsn. (%) |
|---|---|---|---|---|
| U 53 polyurethane | adhesive | 40 | 291 | 99.8 |
| erioglaucine | colorant | 5 | 0.58 | .025 |
| Triton ® W 30 | surfactant | 10 | 1.5 | 0.13 |
| Aervsol ® RM-8 | thickener | 1 | 8.18 | .07 |

TABLE 6

| Peel strength (p.l.i.) | Dielectric surfactant | Sample hematocrit | Filling time(s) after 10[1] or 13[2] weeks under the following storage conditions. | | | |
|---|---|---|---|---|---|---|
| | | | Initial | 4° | 40° | 50° |
| 10.6 | none | 40 | 0.42[1] | 0.28[1] | 0.69[1] | 0.68[1] |
| | .075% L-77 | 40 | 0.32[1] | 0.19[1] | 0.44[1] | 0.75[1] |
| | .05% L-77 | 40 | 0.58[2] | 0.37[2] | 0.77[2] | 0.41[2] |
| | .05% L-77 | 60 | | 0.38[2] | 0.84[2] | 0.54[2] |

These data demonstrate high bond strength and rapid fill times under all storage conditions tested even with extremely high hematocrit blood. The presence of surfactant in the dielectric causes a slight improvement in fill times. This example demonstrates good fill times for both normal and high hematocrit blood even after the sensor was stressed. Four comparison sensors with a reagent layer were assembled using lidstock which had been punched and formed as described but which did not have the bifunctional coating. These sensors were held together by double faced adhesive tape. The fill time for these freshly prepared sensors was more than 11 seconds indicating that the bifunctional coating of the present invention is critical for rapid filling of the capillary space.

EXAMPLE 4

Water Dispersible Polyurethane U53 Combined with Secondary Co-Polymer Airflex® 400 Vinyl-Ethylene Emulsion and Fluorad™ FC99.

The film was prepared and tested as in the first example except that the base had a reaction layer over the printed electrodes. The results are set out in Tables 7 and 8.

TABLE 7

| Component | Function | Concn (%) | Amount (g) | Dry compsn. (%) |
|---|---|---|---|---|
| U 53 polyurethane | adhesive | 40 | 248.2 | 83.1 |
| Airflex ® 400 | adhesive | 50 | 39.6 | 16.6 |
| erioglaucine | colorant | 5 | 0.59 | .025 |
| Fluorad ™ FC 99 | surfactant | 10 | 2.88 | 0.24 |
| Aervsol ® RM-8 | thickener | 1 | 8.71 | .073 |

TABLE 8

| Peel strength (p.l.i.) | Dielectric surfactant | Sample hematocrit | Filling time(s) after 13 weeks under the following storage conditions. | | | |
|---|---|---|---|---|---|---|
| | | | Initial | 4° | 40° | 50° |
| 5.7[1] | .05% L-77 | 40 | 0.66 | 0.55 | 0.27 | 0.76 |
| | .05% L-77 | 60 | 0.91 | 0.51 | 0.36 | 0.79 |

[1]Peel strength measured to dielectric without surfactant.

From the data presented in Tables 7 and 8 it can be determined that a combination of a different surfactant and a different secondary polymer gives excellent fill times with blood of normal and high hematocrit without requiring refrigerated storage.

EXAMPLE 5

Water Dispersible Polyurethane U54 Combined with Elvase® 40722 Vinylacetate-Ethylene Emulsion, Flexbond® 150 Polyvinylacetate Based General Purpose Pressure Sensitive Emulsion, and Surfactant Fluorad FC129.

The data generated using this formulation are set out in Tables 9 and 10.

TABLE 9

| Component | Function | Concn (%) | Amount (g) | Dry Compsn. (%) |
|---|---|---|---|---|
| U 54 polyurethane | adhesive | 50 | 215.7 | 75.5 |
| Flexbond ® 150 | adhesive | 55 | 20.8 | 8.0 |
| Elvace ® 40722 | adhesive | 55 | 41.7 | 16.0 |
| erioglaucine | colorant | 5 | 0.61 | 0.022 |
| Fluorad ™ FC 129 | surfactant | 10 | 4.53 | 0.32 |
| Aervsol ® RM-8 | thickener | 1 | 16.6 | .12 |

TABLE 10

| Peel strength (p.l.i.) | Dielectric surfactant | Sample hematocrit | Filling time(s) after 8 weeks under the following storage conditions. | | | |
|---|---|---|---|---|---|---|
| | | | Initial | 4° | 40° | 50° |
| 9.4 | none | 40 | 0.62 | 0.55 | 0.78 | 0.77 |
| | .05% L-77 | 40 | 0.41 | 0.27 | 0.46 | 0.64 |

This example demonstrates excellent performance with a different water soluble polyurethane.

We claim:

1. An electrochemical sensor for the detection of an analyte in a fluid test sample which comprises:

a) an insulating base plate;

b) an electrode layer on said base plate in operative connection with an enzyme which reacts with the analyte to produce mobile electrons; and c) a lid of deformable material which has been embossed to provide a concave area in a portion thereof while leaving a flat surface surrounding the concave portion in such a configuration that, when mated with the base, the lid and base form a capillary space in which the enzyme is available for direct contact with fluid test sample which is drawn into the capillary space by capillary action, wherein said sensor has a polymeric layer over the underside of the lid to facilitate bonding of the lid to the base upon their being mated and to increase the hydrophilic nature of the capillary space.

2. The sensor of claim 1 wherein the polymeric layer comprises a surfactant stabilized polyurethane.

3. The sensor of claim 1 wherein the polymer layer comprises a water dispersible polyurethane ionomer.

4. The sensor of claim 3 wherein the polyurethane ionomer is anionic.

5. The sensor of claim 4 wherein the polyurethane ionomer is a linear aliphatic polyester urethane based on hexamethylene diisocyanate and isophorone diisocyanate.

6. The sensor of claim 1 wherein the polymer is a vinylacetate-ethylene co-polymer.

7. The sensor of claim 1 wherein there is an electrical conducting layer on the surface of the insulating base plate and the electrode layer is on the surface of the conducting layer and in electrically conductive contact therewith.

8. The sensor of claim 1 wherein the lid is mated to the base with direct contact between the lid and the base being at the electrode surface and the under side of the lid.

9. The sensor of claim 1 wherein there is a layer of dielectric material patterned over the electrode layer so that only a portion of the electrode, as predetermined by the pattern of the dielectric layer, is available for direct contact with the fluid test sample.

10. The sensor of claim 9 wherein the lid is configured so that its edges mate with the dielectric layer.

11. The sensor of claim 9 wherein the dielectric layer is configured so that it leaves a portion of the electrode layer exposed for direct contact with the flat surfaces of the lid.

12. The sensor of claim 1 wherein the enzyme is an oxidoreductase.

13. A method of making an electrochemical sensor for the detection of an analyte in a fluid test sample which comprises:

a) providing an insulating base plate which has on its surface an electrode layer in operative connection with an enzyme which reacts with the analyte to produce mobile electrons; and b) mating the base plate with a lid of a deformable material a part of which encompasses a concave area with a flat surface surrounding the concave portion in such a configuration that, when mated with the base, the lid and base form a capillary space in which the enzyme is available for direct contact with the fluid test sample in the capillary space and the lid has a polymeric layer over the underside thereof to facilitate bonding of the lid to the base and increase the hydrophilic nature of the capillary space; and c) heating the base plate and lid while applying pressure therebetween to fuse the base plate to the lid.

14. The method of claim 13 wherein there is a layer of dielectric material patterned over the electrode layer so that only a portion of the electrode, as predetermined by the pattern of the dielectric layer, is available for direct contact with the fluid test sample.

15. The method of claim 13 wherein the dielectric layer is configured so that the flat surfaces of the lid mate solely with the dielectric layer.

16. The method of claim 13 wherein the dielectric layer is configured so that it leaves at least a portion of the electrode layer exposed for direct contact with the flat surfaces of the lid.

17. The method of claim 13 wherein the polymeric layer on the underside of the lid comprises a surfactant stabilized polyurethane.

18. The method of claim 13 wherein the polymer layer comprises a water dispersible polyurethane ionomer.

19. The method of claim 18 wherein the polyurethane ionomer is anionic.

20. The method of claim 19 wherein the anoinic polyurethane ionomer is a linear aliphatic polyester urethane based on hexamethylene diisocyanate and isophorone diisocyanate.

* * * * *